(12) United States Patent
Murray et al.

(10) Patent No.: US 8,855,747 B2
(45) Date of Patent: Oct. 7, 2014

(54) ENGAGED FIDUCIALS AND SYSTEM FOR DEPLOYMENT

(71) Applicant: Cook Medical Technologies LLC, Bloomington, IN (US)

(72) Inventors: Mark Murray, Co. Westmeath (IE); Triona Campbell, Co. Clare (IE); Vincent McHugo, Co. Tipperary (IE); Michael Clancy, Limerick (IE); John Neilan, Co. Galway (IE)

(73) Assignee: Cook Medical Technologies LLC, Bloomington, IN (US)

( * ) Notice: Subject to any disclaimer, the term of this patent is extended or adjusted under 35 U.S.C. 154(b) by 4 days.

(21) Appl. No.: 13/645,614

(22) Filed: Oct. 5, 2012

(65) Prior Publication Data

US 2013/0096427 A1    Apr. 18, 2013

Related U.S. Application Data

(60) Provisional application No. 61/546,776, filed on Oct. 13, 2011.

(51) Int. Cl.

| | | |
|---|---|---|
| *A61B 6/00* | (2006.01) | |
| *A61M 36/12* | (2006.01) | |
| *A61B 5/055* | (2006.01) | |
| *A61B 17/34* | (2006.01) | |
| *A61N 5/10* | (2006.01) | |
| *A61B 19/00* | (2006.01) | |
| *A61B 17/00* | (2006.01) | |

(52) U.S. Cl.
CPC ............... *A61B 19/54* (2013.01); *A61N 5/1027* (2013.01); *A61N 5/1049* (2013.01); *A61B 2019/5466* (2013.01); *A61B 2019/5491* (2013.01); *A61B 2019/5425* (2013.01); *A61B 17/3468* (2013.01); *A61N 5/1001* (2013.01); *A61B 2019/5487* (2013.01); *A61B 2017/00477* (2013.01)
USPC ............................... 600/433; 600/7; 600/414

(58) Field of Classification Search
USPC ................. 600/7, 8, 414, 420, 431, 432, 567; 128/898; 604/116
See application file for complete search history.

(56) References Cited

U.S. PATENT DOCUMENTS

| | | | |
|---|---|---|---|
| 6,220,248 B1 | 4/2001 | Voegele et al. | |
| 6,264,599 B1 | 7/2001 | Slater et al. | |

(Continued)

FOREIGN PATENT DOCUMENTS

| | | | |
|---|---|---|---|
| WO | WO 97/19724 A1 | 6/1997 | |
| WO | WO 2007/094001 A2 | 8/2007 | |

(Continued)

OTHER PUBLICATIONS

International Search Report for International Application No. PCT/US2012/058679, dated Jan. 2, 2013, 3 pages.

*Primary Examiner* — Michael Rozanski
(74) *Attorney, Agent, or Firm* — Brinks Gilson & Lione (57) ABSTRACT

Embodiments include a fiducial deployment system including a needle and at least two adjacent and releasably-engaged fiducials retained within a lumen of the needle by engagement with each other and/or by engagement with a pusher element. A fiducial may include one or more mechanical engagement structures that interengage with and/or are rupturably attached to one or more adjacent fiducials. The needle, which may include echogenic enhancements, may be configured to deliver a plurality of fiducials to a target location in serial fashion, one at a time. A variety of releasably-engaged fiducials are disclosed, as are methods for use.

26 Claims, 5 Drawing Sheets

(56) References Cited

U.S. PATENT DOCUMENTS

| | | |
|---|---|---|
| 7,565,191 B2 | 7/2009 | Burbank et al. |
| 2009/0131734 A1* | 5/2009 | Neustadter et al. ............... 600/8 |
| 2010/0331677 A1* | 12/2010 | Hong et al. ................... 600/432 |

FOREIGN PATENT DOCUMENTS

| WO | WO 2007/103204 A2 | 9/2007 |
|---|---|---|
| WO | WO 2009/132349 A2 | 10/2009 |

* cited by examiner

ENGAGED FIDUCIALS AND SYSTEM FOR DEPLOYMENT

CROSS-REFERENCE TO RELATED APPLICATIONS

This application claims priority to U.S. Provisional Application Ser. No. 61/546,776, filed Oct. 13, 2011, which is incorporated herein by reference in its entirety.

TECHNICAL FIELD

The invention relates generally to a medical device system including one or more fiducials and methods of use for same. More particularly, the invention pertains to specially-configured fiducials, needles configured for use with them, and methods of use for same.

BACKGROUND

Medical procedures often require locating and treating target areas within a patient. Focused, dose-delivery radiation therapy requires locating the target with a high degree of precision to limit damaging healthy tissue around the target. It is particularly important to know or estimate the precise location of the target in radiation oncology because it is desirable to limit the exposure of adjacent body parts to the radiation in a patient already suffering the depredations of cancer. However, in all treatment procedures, whether radiologic or otherwise, it is most desirable to be able to accurately target a region to be treated.

In many applications, it is not possible to directly view a treatment target or portion thereof (such as, for example, a cancerous tumor, cyst, pseudocyst, or other target) that needs to be acted on in some manner. As one example, when treating a lung or pancreatic tumor with radiation, it may not be possible to view the actual tumor within the patient immediately before the radiation treatment. It is therefore highly advantageous to have some mechanism for permitting the tumor to be located accurately so that the radiation treatment can be targeted at the tumor while avoiding damage to healthy tissue.

Even for target regions that may be visualized using CAT (computer-assisted tomography) scans, MRI (magnetic resonance imaging), x-rays, ultrasound, or other techniques, difficulties often arise in targeting a treatment. This is particularly true for target regions within a torso of a patient and soft tissue regions. Due to the mobility of tissues in those regions (e.g., movement of internal organs during respiration and/or digestion, the movement of breast tissue with any change of body position), a target region may not remain fixed relative to anatomical landmarks and/or to marks that can be placed onto an external surface of a patient's body during one of those visualization procedures.

Several techniques have been developed to address this problem. One such technique is to place markers into the patient along the margins of the target region. The markers may be active (e.g., emitting some kind of signal useful in targeting a therapy) or passive (e.g., non-ferromagnetic gold markers—called fiducials—that can be used for targeting under ultrasound, MRI, x-ray, or other targeting techniques, which may be included in a treatment device).

A fiducial is typically formed of a radio-opaque material so that the target can be effectively located and treated with a device that targets a site using the fiducials as positional markers under radiographic detection. Typically, the fiducials may be inserted into the patient during a simple operation. Percutaneous placement is most commonly used. However, use of minimally-invasive placement via an endoscope has recently developed for fiducial placement into a patient's internal organs. For example, percutaneous placement of fiducials along the margins of a pancreatic tumor can be complex and painful (particularly for obese patients, where the needle size is necessarily larger). Another process using percutaneously implanted objects in a patient is brachytherapy. In brachytherapy, radioactive sources or "seeds" are implanted into and/or adjacent a tumor to provide a high dose of radiation to the tumor, but not the healthy tissue surrounding the tumor.

Figure 1A:
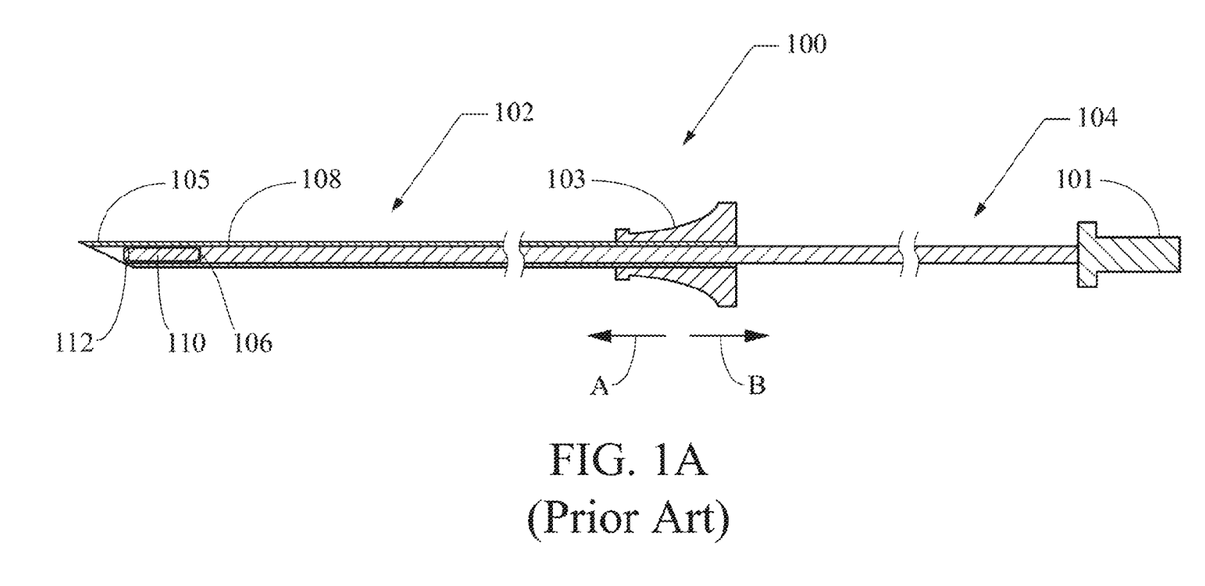
FIGS. 1A-1B show a prior art fiducial introducer and method of use.
Figure 1B:
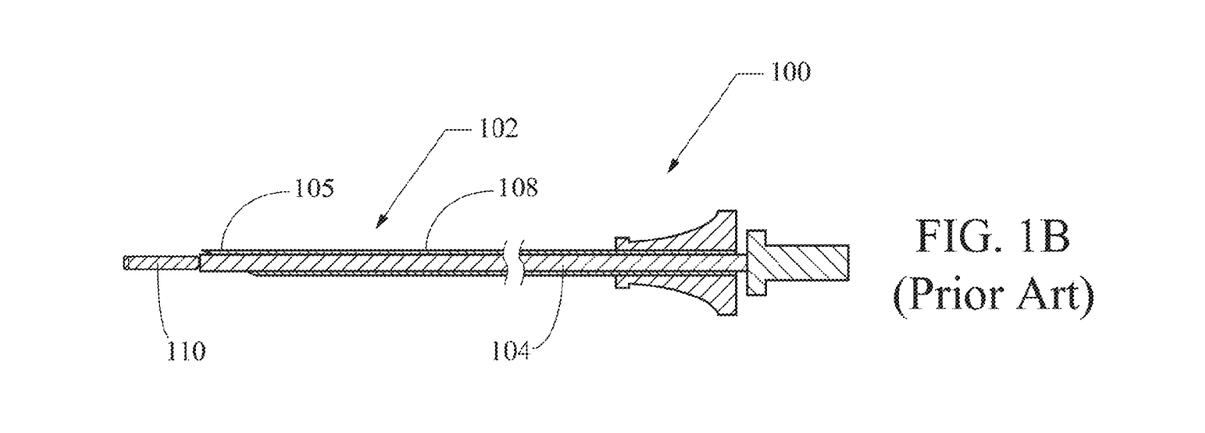

FIGS. 1A and 1B show longitudinal sectional views of a two-piece introducer 100 of the prior art useful for placement of brachytherapy seeds or fiducials. Referring first to FIG. 1A, the introducer 100 includes a needle 102 and a stylet 104 slidably disposed within the needle 102. The stylet 104 includes a first handle 101 and a blunt distal end 106. The needle 102 includes a second handle 103 and a bevel-tipped cannula 108 extending through the second handle 103. The cannula 108 is configured to hold a seed/fiducial 110. The cannula 108 has a distal tip 105 configured for percutaneous implantation of the seed/fiducial 110 into the patient.

In a "pre-loaded configuration," the seed/fiducial 110 is retained in the cannula 108 by a plug 112 made from bone wax or other suitable bio-compatible material(s). This is typically accomplished by a "muzzle-loading" technique where the fiducial is placed into the distal end of the needle and then held in place by the bone wax plug. This can present some challenges, as the bone wax plug 112 can be visible as an artifact in the patient, potentially interfering with clear visualization of body structures or treatment devices. With this configuration, the cannula 108 must be withdrawn and reloaded after delivery of each seed/fiducial 110. If the target locations for the fiducials are very far apart, use of a single percutaneous introducer cannula/trocar for multiple introductions of the cannula 108 may not be possible. In such a circumstance, the patient must endure several percutaneous punctures (and the increased attendant risk of infection for each).

To implant the desired arrangement of seeds/fiducials 110 at a target location in a patient, an operator pushes the cannula 108 in a first direction (arrow A) to insert the tip 105 into the patient (typically under fluoroscopic visualization). The operator then pushes the second handle 103 further in the first direction to position the tip 105 at the desired depth within the patient where a seed/fiducial 110 is to be implanted. Throughout this motion, the operator moves the needle 102 and the stylet 104 together as a unit. At the desired depth/location, the operator grasps the first handle 101 with one hand and the second handle 103 with the other hand. Then, the operator holds the first handle 101 stationary while simultaneously sliding the second handle 103 back in a second direction (arrow B) toward the first handle 101. As shown in FIG. 1B, this movement causes the cannula 108 to retract over the seed/fiducial 110 to implant it in the patient. Alternatively, the operator may move the first handle 101 in the first direction (arrow A) while sliding the second handle 103 back in the second direction (arrow B) or holding it stationary. This causes the stylet 104 to push the seeds 110 out of the cannula 108. The procedure is then repeated to place other seeds/fiducials 110. When being used for targeting of radiation therapy, a minimum of three fiducials is typically required.

As will be appreciated from the disclosed structure, after deploying one fiducial, one may alternatively reload the introducer 100 from the proximal end by completely withdrawing the stylet 104, then placing another fiducial into the needle lumen and advancing it therethrough to a second location to which the distal needle tip 105 has been directed (a "breech-loading" technique). Provided that the fiducial target sites are sufficiently close together to allow this technique, it can reduce the number of percutaneous punctures or other access procedures needed to place more than one fiducial. However, it creates a problem for procedures where ultrasound is being used or is to be used in the near-future because it introduces air pockets into the tissue and related fluids. Those air pockets with tissue and/or fluid are echogenic in a manner that can interfere with ultrasound visualization of a target area and/or tools being used to diagnose or treat in/around the area. In some brachytherapy techniques, a series of fiducials may be preloaded into the needle—either separately or connected by a suture or similar device—then placed together in fairly close proximity; however, such a technique typically is not effective for placing three or more fiducials in sufficiently disparate locations to use for targeting a treatment relative to, for example, margins of a tumor.

The process is similar when implemented endoscopically in the manner developed rather recently, except that the needle and stylet are of the type known in the art for use through the working channel of an endoscope. One limitation of current endoscopic techniques is the size of fiducial that can be introduced. With the size limitation of endoscope working channels, the largest needle that can typically be used without risking bending, crimping, curving or otherwise damaging a needle (that does not have an internal stylet or other support) during advancement out of the endoscope to an anatomical target is a 19-gauge needle. This limits the size of the fiducial that can be introduced through the needle lumen using current, cylindrical fiducials. The endoscopic technique generally suffers from the same reloading problems as described above. Even though the external percutaneous punctures are not an issue, having to withdraw and reload takes up valuable time and complicates the procedure, potentially requiring additional personnel, whether only the stylet is withdrawn for "breech-loading" or the entire device is withdrawn for "muzzle-loading."

It would be desirable to use ultrasound, and particularly endoscopic ultrasound (EUS) for navigation and placement of fiducials. As such it would be desirable to provide and use the largest possible fiducial that will provide improved echogenicity based on its size and echogenic profile. It would be desirable to provide multiple fiducials in a needle that can be introduced in a controlled serial manner (one at a time) rather than requiring manual reloading after placement of each fiducial.

BRIEF SUMMARY

Embodiments of a fiducial deployment system described herein may include at least one first fiducial and at least one second fiducial, where the at least one first fiducial is engaged with the at least one second fiducial; where the at least one first fiducial and the at least one second fiducial are disposed along a common collinear axis; and where the distal region aperture, the at least one first fiducial, and the at least one second fiducial are configured such that advancing the at least one first fiducial through the distal region aperture will facilitate disengagement of the at least one first fiducial from the at least one second fiducial. The engagement may be configured as a mechanical interengagement where portions of the fiducial engagingly overlap, as a rupturable connection between adjacent fiducials, any combination thereof, or as another form of releasable engagement.

DETAILED DESCRIPTION

The terms "proximal" and "distal" are used herein in the common usage sense where they refer respectively to a handle/doctor-end of a device or related object and a tool/patient-end of a device or related object. Certain embodiments may be configured for placement of fiducials through an endoscope. More particularly, in certain embodiments, a fiducial placement system may be configured of sufficient length and flexibility for use and actuation through a working channel of a gastrointestinal endoscope providing access to the gastrointestinal tract and/or adjacent structures in a patient body. Those of skill in the art will appreciate that fiducials and deployment system embodiments described herein may be useful for percutaneous introduction (e.g., for targeted treatment of breast cancer) within the scope of the present disclosure and claims.

A fiducial deployment system 200 is described with reference to FIGS. 2A-2B. The system 200 includes a needle 202 that includes a generally tubular cannula body 208, shown in longitudinal section. The cannula body 208 in this embodiment includes a beveled distal tip 205 configured for penetrating tissue and directing the cannula's contents to a target location, but other embodiments may include non-beveled tips or other designs. The cannula body 208 defines a needle lumen 206 that extends longitudinally through at least a lengthwise portion of the cannula body to a distal region aperture, illustrated as a needle end opening 207 that generally defines a distal terminus of the cannula body 208.

An outer surface of the cannula body 208 may be dimpled or otherwise configured to enhance its ability to reflect ultrasound waves and thereby provide a desirable echogenic profile. A dimpled characteristic may be embodied as any type of different irregular, patterned, or textured surface feature (e.g., knurled, ribbed) that may enhance the echogenicity of the cannula body 208. Such enhanced echogenicity will aid in visualizing the cannula body 208 during EUS-guided placement, and allow it to be used in ultrasound visualization of a target site (e.g., a tumor) being marked by one or more fiducials. Other echogenic enhancements may be provided in addition to, or instead of, the dimpling. For example, certain echogenic polymers may be used in the cannula construction, or as a coating of a metal cannula. Other echogenic enhancements known in the art may be implemented within the scope of the claims. The dimpled or otherwise echogenically-enhanced region preferably will include a distal needle end region, while a more proximal length of the needle may be free of dimples and/or other echogenicity-enhancing features.

At least one substantially inflexible ramp structure is provided as a protrusion extending radially in the needle lumen 206. The ramp structure of FIGS. 2A-2B is embodied as an indent or dimple 210 that is oriented near and at least partially opposite the distal region aperture 207. In other embodiments, the dimple 210 may not include an externally visible dimple, and/or it may include one, two, three, or more protrusions into the needle lumen 206. In still other embodiments, a needle embodiment may not include any protrusion, such that the needle lumen includes a substantially consistent inner diameter for substantially its entire length, or for its entire length.

At least one fiducial, embodied here as a plurality of fiducials 220 may be included in the needle lumen 206. Each of the fiducials 220 includes a generally columnar body slidably disposed in the needle lumen 206. The fiducial body may be substantially solid, substantially hollow, or otherwise configured in any manner appropriate for providing a desirable fluoroscopic identifiability of the fiducial 220. Fiducials 220 (and other fiducial embodiments described below) preferably will be formed of a radio-opaque, non-ferromagnetic material such as, for example, gold, platinum, palladium, iridium, rhenium, tantalum, or alloys thereof. One preferred embodiment may include an alloy of palladium with rhenium, advantages of which may include desirable radio-opacity, market-price stability superior to gold, and ultrasound-reflectivity/echogenicity due to density. Being radio-opaque will allow the fiducial to be used in deployment techniques using fluoroscopy, as well as make it detectible/visualizable by radiographic means during a treatment or other procedure where it may be desirable to know the location(s) of one or more fiducials. Being non-ferromagnetic will lessen the likelihood that visualization techniques or other procedures employing magnetic fields such as, for example, MRI, will re-orient or otherwise dislodge a fiducial. Echogenic properties of a fiducial or needle may be enhanced by surface texture, but can also be provided by structural inclusions such as embedded bubbles or beads that provide for a different ultrasound reflectivity than material surrounding them. Fiducials may also be coated with a material (e.g., parylene) configured to reduce backscatter during radiography.

Figure 2A:
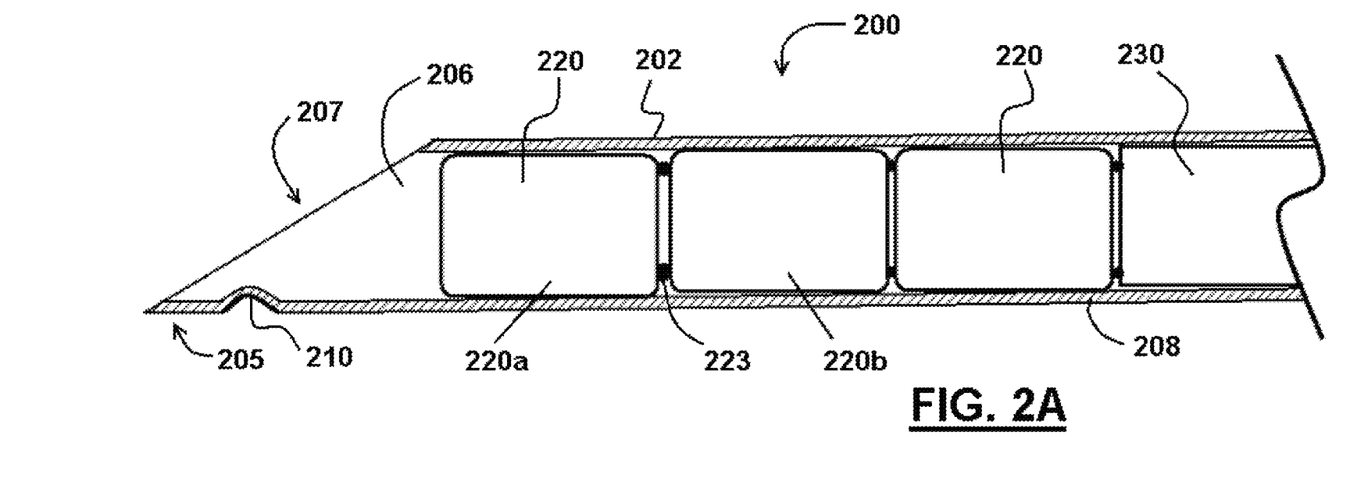
FIGS. 2A-2B show one embodiment of a fiducial deployment system.
Figure 2B:
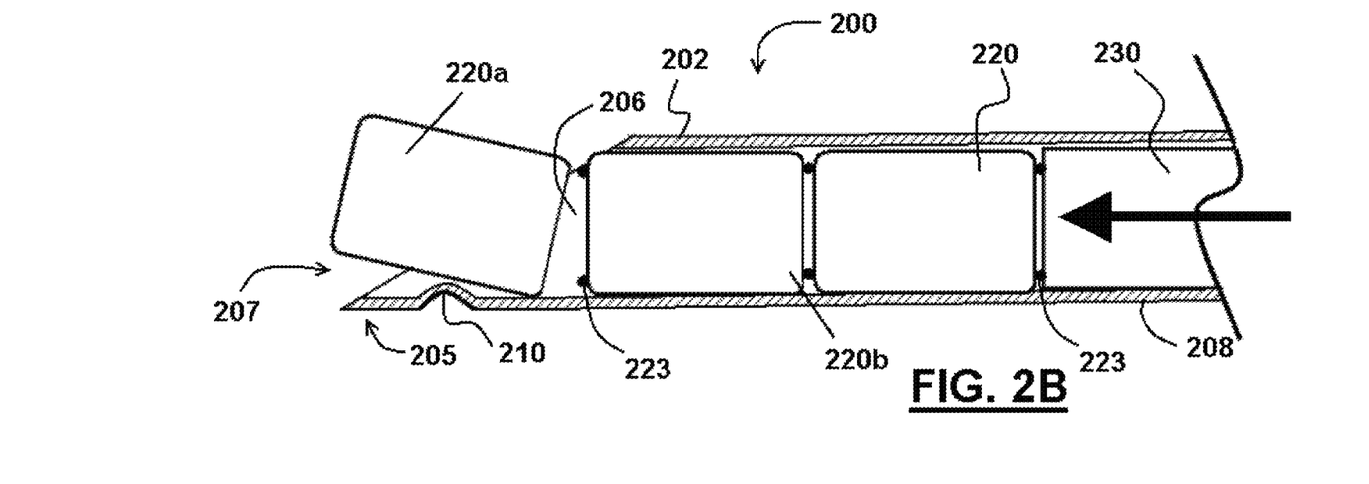

In the embodiment of FIGS. 2A-2B, the fiducials 220 include at least one first fiducial 220a (shown as the distal-most fiducial) and at least one second fiducial 220b. The first fiducial 220a is immediately adjacent and engaged with the second fiducial 220b, and the first and second fiducials 220a, 220b are disposed along a common collinear longitudinal axis. This axis may be straight or curved, depending upon the orientation of the cannula body 208 and its lumen 206. If the cannula body 208 is flexible, then the common collinear axis of the fiducials 220a, 220b may be curved as it follows curvature of the cannula body 208.

The engagement of the first fiducial 220a to the second fiducial 220b may include at least one attachment by a rupturable material 223. The rupturable material may be breakable (e.g., mechanically rupturable), dissolvable, or otherwise rupturable in a manner allowing the engaged fiducials to separate. The embodiment of FIGS. 2A-2B contemplates a mechanically rupturable material 223. It is preferable that the connection formed by the material 223 be sufficiently robust that it will not be disrupted in a manner disengaging the fiducials from each other or the stylet 230 during normal flexure and manipulation of the cannula body 208 while the fiducials 220 are within the needle lumen 206.

The mechanically rupturable material 223 may connect the first and second fiducials 220a, 220b at a single point, at a plurality of points, or along one or more seams. Preferred mechanically rupturable materials 223 may be brittle and non-elastic. Specific examples of suitable materials include scored, perforated, unscored, unperforated, or otherwise structured polymeric, metallic, or other materials known in the art to be rupturable without releasing particles of material. This engagement allows for the system 200 to be used for serial, one-at-a-time release of fiducials 220.

As shown in FIGS. 2A-2B, each successive fiducial 220 may be engaged with the one in front of it. A pusher stylet 230 may also be disposed through the needle lumen 206. The proximal-most fiducial 220 may be engaged with the stylet 230 in a manner configured substantially similarly to, identical to, or different than the connecting means that engages any of the fiducials 220 that are distal of the stylet 230. This configuration will allow a user to advance the fiducials 220 distally or retract them proximally while they are attached to each other and to the stylet 230. The engaged fiducials are configured to separatingly disengage when, for example, the first fiducial 220a is angularly offset out of the collinear axis it shares with the second fiducial 220b such that the rupturable material 223 attaching them together is ruptured and breaks.

A method of fiducial deployment using the system 200 is described with reference to FIGS. 2A-2B, which show the fiducials 220 engaged with each other and with the stylet 230 by a mechanically rupturable material 223. In FIG. 2A, the fiducials 220 are attached together and aligned along a shared collinear axis. In FIG. 2B, the stylet 230 has been advanced distally to deploy the distalmost first fiducial 220a. This deployment is effected as the distalmost first fiducial 220a is advanced distally over the ramp structure formed by the dimple 210. As the first fiducial 220a contacts and is advanced over the dimple 210, that fiducial 220a is directed angularly out of the collinear axis it shared with the next fiducial 220b, and the connecting material 223 is ruptured and breaks. This releases and deploys the first fiducial 220a out through the distal needle aperture 207.

Other fiducial embodiments for the system described with reference to FIGS. 2A-2B (and FIGS. 3A-3B) may be practicable with the structures described herein. For example, the shape of the distal leading end of a fiducial may provide a certain ease or advantage in advancing the fiducial(s) over and past a ramp or other protrusion. As one example, a fiducial with a blunt cylindrical distal end may be more difficult to advance toward and past a protrusion 210 than a fiducial with a radiused, chamfered, rounded, beveled, or otherwise shaped distal end configured to ease passage across said protrusion. A distal end of one or more fiducials may be partially rounded or beveled to correspond with a beveled needle end. It should be appreciated that fiducial configurations shown in FIGS. 5-6 and other fiducial configurations may be used with the systems described herein. It should be appreciated that the particular shapes, surface positions on fiducial bodies, and general proportions of these and the other protuberances disclosed herein may be interchanged or otherwise modified within the scope of the claims, including with reference to other fiducial designs such as those disclosed in U.S. patent application Ser. Nos. 12/764,432 and 12/964,062, each of which is incorporated herein by reference. The generally columnar construction of fiducials described herein includes a broad variety of potential geometries within the scope of the claims, including for example regular and irregular geometric shapes having rounded and/or polyhedral borders and cross-sections. In some preferred embodiments, at least one fiducial will include a generally cylindrical body portion.

A fiducial deployment system 300 is described with reference to FIGS. 3A-3B. The system 300 includes a needle 302 that includes a generally tubular cannula body 308. The cannula body 308 in this embodiment includes a beveled distal tip 305 configured for penetrating tissue and directing the cannula's contents to a target location, but other embodiments may include non-beveled tips or other designs. The cannula body 308 defines a needle lumen 306 that extends longitudinally through at least a lengthwise portion of the cannula body to a distal region aperture, illustrated as a needle end opening 307 that is open to a lateral side of the cannula body 308 and proximal of the distal terminus of the cannula body 308. Stated differently, the distal region aperture 307 is offset from a longitudinal axis defined by a major length of the needle lumen 306. In the illustrated embodiment, the aperture 307 is generally parallel with that axis. In other embodiments, it may be oriented at an oblique angle thereto.

At least one substantially inflexible ramp structure 310 is provided as a protrusion extending radially in the needle lumen 306. The ramp structure of FIGS. 3A-3B is embodied as solid ramp 310 that is oriented near and at least partially opposite the distal region aperture 307. The ramp includes a lumen-facing surface 310a that is generally contiguous with and extends into a columnar surface generally defined by the needle lumen 306. The body of the ramp 310 occludes the distal needle terminus of this embodiment, such that the lumen 306 turns upward at its distal end to terminate in the needle end opening 307.

An outer surface of the cannula body 308 may be dimpled or otherwise configured to enhance its ability to reflect ultrasound waves and thereby provide a desirable echogenic profile. A dimpled characteristic may be embodied as any type of surface feature, such as those described above with respect to the fiducial deployment system 200, that may enhance the echogenicity of the cannula 308.

At least one fiducial, embodied here as a plurality of fiducials 320 may be included in the needle lumen 306. Each of the fiducials 320 includes a generally columnar body slidably disposed in the needle lumen 306. The fiducial body may be substantially solid, substantially hollow, or otherwise configured in any manner appropriate for providing a desirable fluoroscopic identifiability of the fiducial 320. The fiducials 320 may be configured to include a beveled, rounded, or otherwise contoured distal end that will facilitate distal-ward passage through the lumen 306, up the ramp 310, and out through the distal region aperture 307.

Figure 3A:
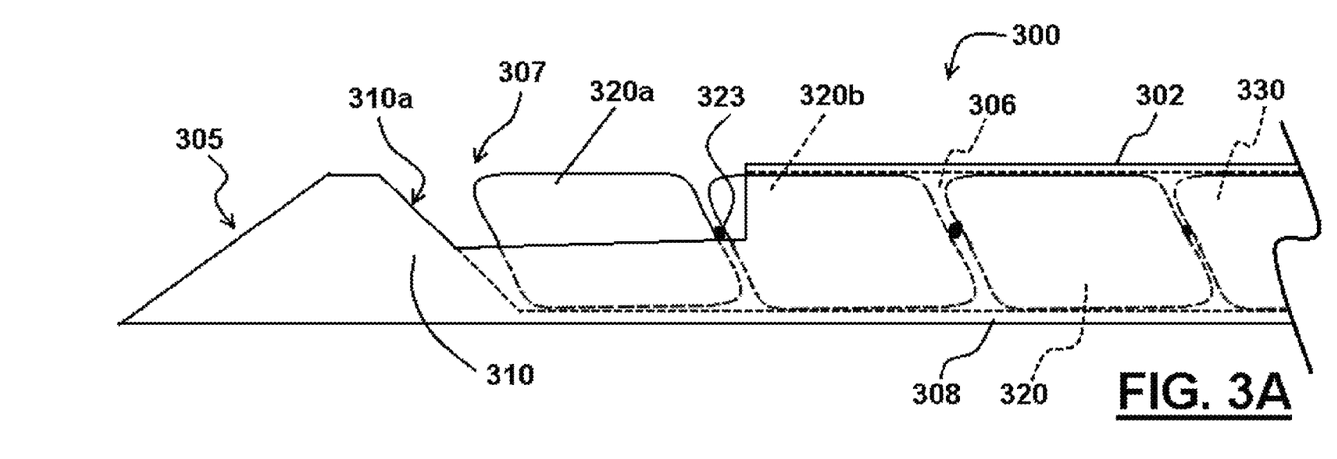
FIGS. 3A-3B show another embodiment of a fiducial deployment system.
Figure 3B:
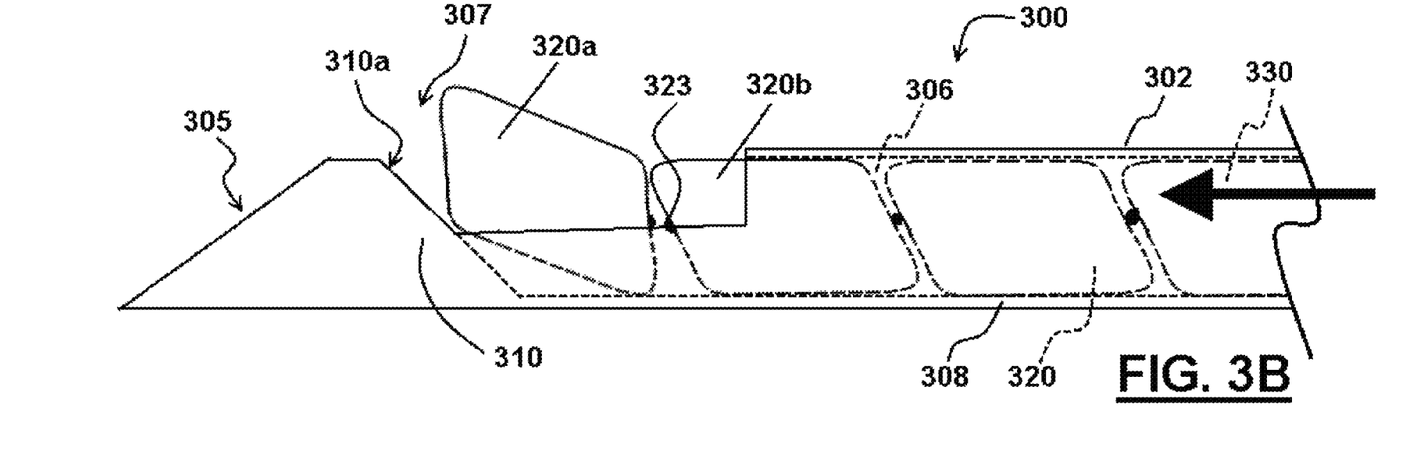

In the embodiment of FIGS. 3A-3B, the fiducials 320 include at least one first fiducial 320a (shown as the distalmost fiducial) and at least one second fiducial 320b. The first fiducial 320a is immediately adjacent and engaged with the second fiducial 320b, and the first and second fiducials 320a, 320b are disposed along a common collinear axis. This axis may be straight or curved, depending upon the orientation of the needle body 308 and its lumen 306. If the needle body 308 is flexible, then the common collinear axis of the fiducials 320a, 320b may be curved as it follows curvature of the needle body 308.

The engagement of the first fiducial 320a to the second fiducial 320b may include at least one attachment by a rupturable material 323. The rupturable material may be breakable (e.g., mechanically rupturable), dissolvable, or otherwise rupturable in a manner allowing the engaged fiducials to separate. The embodiment of FIGS. 3A-3B contemplates a mechanically rupturable material 323. It is preferable that the connection formed by the material 323 be sufficiently robust that it will not be disrupted in a manner disengaging the fiducials from each other or the stylet 330 during normal flexure and manipulation of the cannula body 308 while the fiducials 320 are within the needle lumen 306.

The mechanically rupturable material 323 may connect the first and second fiducials 320a, 320b at a single point, at a plurality of points, or along one or more seams. Preferred mechanically rupturable materials 323 may be brittle and non-elastic. Specific examples of suitable materials include those described above with reference to FIGS. 2A-2B, and—like the embodiment of those figures—may include other materials. This engagement allows for the system 300 to be used for serial, one-at-a-time release of fiducials 320.

As shown in FIGS. 3A-3B, each successive fiducial 320 may be engaged with the one in front of it. A stylet 330 may also be disposed through the needle lumen 306. The proximal-most fiducial 320 may be engaged with the stylet 330 in the same, a substantially similar, or a different manner than the engagement between any of the fiducials 320 that are distal of the stylet 330. This configuration will allow a user to advance the fiducials 320 distally or retract them proximally while they are attached to each other and to the stylet 330. The engaged fiducials are configured to separatingly disengage when, for example, the first fiducial 320a is angled out of the collinear axis it shares with the second fiducial 320b such that the rupturable material 323 attaching them is ruptured and breaks.

A method of fiducial deployment using the system 300 is described with reference to FIGS. 3A-3B, which show the fiducials 320 engaged with each other and with the stylet 330 by a mechanically rupturable material 323. In FIG. 3A, the fiducials 320 are attached together and aligned along a shared collinear axis. In FIG. 3B, the stylet 330 has been advanced distally to partially deploy the distalmost first fiducial 320a. This deployment will be fully effected as the distalmost first fiducial 320a is advanced distally over the ramp structure 310. As the first fiducial 320a contacts and is advanced over the ramp 310, that fiducial 320a is directed angularly out of the collinear axis it shared with the second fiducial 320b. As the first fiducial 320a is angularly offset relative to the second fiducial 320b, the connecting material 323 breaks. This releases and allows the first fiducial 320a to be deployed by being advanced (by the stylet and trailing fiducials) out through the distal needle aperture 307. As described above, this process can be repeated until some desired plurality of fiducials has been deployed, most likely with the needle having been repositioned to a new location prior to each deployment, but preferably without requiring any reloading of the needle with additional fiducials.

A fiducial deployment system 400 is described with reference to FIGS. 4A-4B. The system 400 includes a needle 402 that includes a generally tubular cannula body 408, shown in longitudinal section. The cannula 408 in this embodiment includes a beveled distal tip 405 configured for penetrating tissue and directing the cannula's contents to a target location, but other embodiments may include non-beveled tips or other designs. The cannula body 408 defines a needle lumen 406 that extends longitudinally through at least a lengthwise portion of the cannula body to a distal region aperture, illustrated as a needle end opening 407 that generally defines a distal terminus of the cannula body 408.

An outer surface of the cannula body 408 may be dimpled or otherwise configured to enhance its ability to reflect ultrasound waves and thereby provide a desirable echogenic profile. A dimpled characteristic, shown here as dimples 409, may be embodied as any type of different irregular, patterned, or textured surface feature (e.g., knurled, ribbed) that may enhance the echogenicity of the cannula body 408. Such enhanced echogenicity will aid in visualizing the cannula body 408 during EUS-guided placement, and allow it to be used in ultrasound visualization of a target site (e.g., a tumor) being marked by one or more fiducials. Other echogenic enhancements may be provided in addition to, or instead of, the dimpling. For example, certain echogenic polymers may be used in the cannula construction, or as a coating of a metal cannula. Other echogenic enhancements known in the art may be implemented within the scope of the claims. The dimpled or otherwise echogenically-enhanced region preferably will include a distal needle end region, while a more proximal length of the needle may be free of dimples and/or other echogenicity-enhancing features.

At least one fiducial, embodied here as a plurality of fiducials 420 may be included in the needle lumen 406. Each of the fiducials 420 includes a generally columnar body slidably disposed in the needle lumen 406. The fiducial body may be substantially solid, substantially hollow, or otherwise configured in any manner appropriate for providing a desirable fluoroscopic identifiability of the fiducial 420.

Figure 4A:
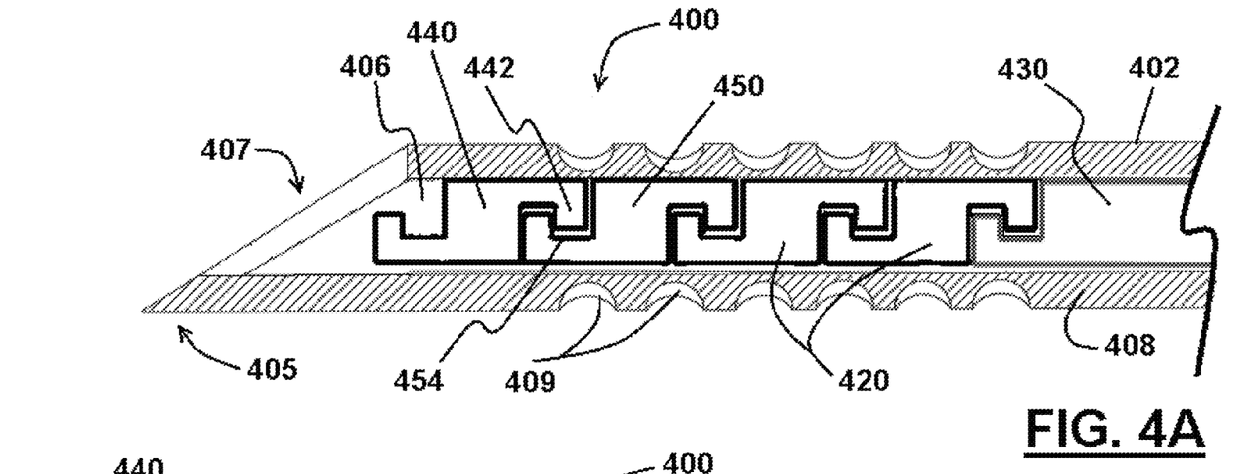
FIGS. 4A-4B show still another embodiment of a fiducial deployment system.
Figure 4B:
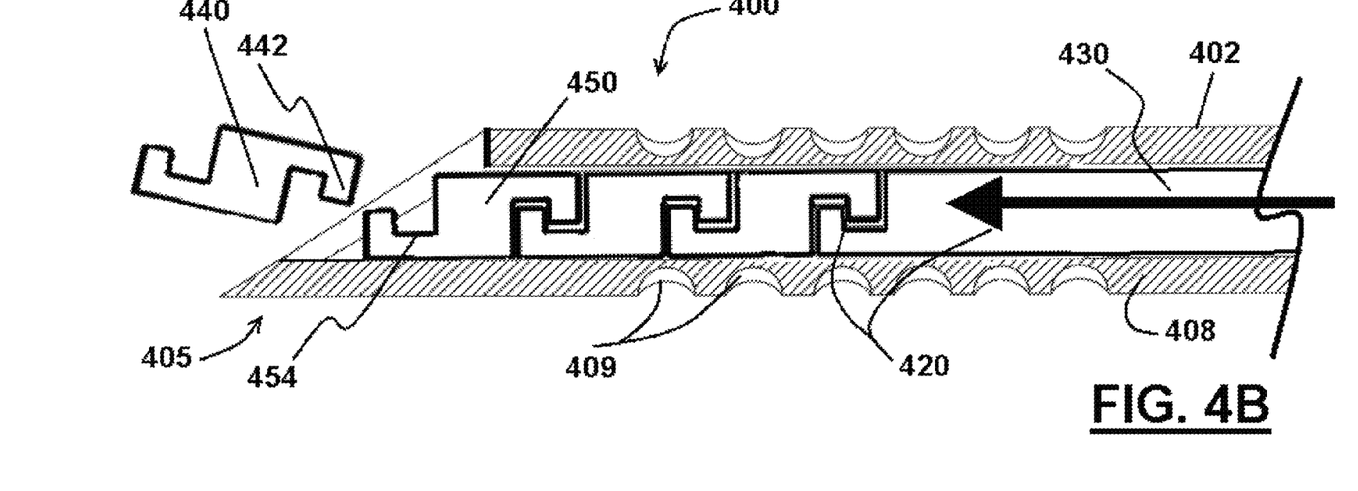

In the embodiment of FIGS. 4A-4B, the fiducials 420 include at least one first fiducial 440 (shown as the distal-most fiducial) and at least one second fiducial 450. The first fiducial 440 is immediately adjacent and engaged with the second fiducial 450, and the first and second fiducials 440, 450 are disposed along a common collinear axis. This axis may be straight or curved, depending upon the orientation of the cannula body 408 and its lumen 406. If the cannula body 408 is flexible, then the common collinear axis of the fiducials 440, 450 may be curved as it follows the curvature of the cannula body 408.

The engagement of the first fiducial 440 to the second fiducial 450 may include at least one attachment by a mechanical interlocking engagement. The first and second fiducials 440, 450 each include a generally S-shaped configuration (that may be, for example, a "block S" as shown, a more rounded S-shape, or any other shape configured to engage with another shaped fiducial adjacent to it). A proximal protrusion 442 of the distal-most first fiducial 440 engages a recess 454 of the second fiducial 450. This engagement may be duplicated or reversed between these two fiducials and successive fiducials, such that—generally—engagement of a first fiducial with a second fiducial comprises at least one of the first fiducial and the second fiducial including a protrusion that engages a recess of the other fiducial. Those of skill in the art will appreciate that a variety of different configurations will provide for such an engagement within the scope of the device described and claimed herein. They will also appreciate that such interengaging protrusions may provide a beneficial migration-reducing and/or migration-prevention function for each fiducial.

The engagement most preferably is configured to be releasably interlocking such that when the engaged portions of adjacent fiducials are not constrained (e.g., within the needle lumen) the distal-most fiducial is released from the engagement. The engagement of successive fiducials may be configured the same way or with a different connection (e.g., mechanical interengagement and/or an attachment of the kind described with reference to FIGS. 2A-3B above. It is preferable that the connection formed by the engagement be sufficiently robust that it will not be disrupted in a manner disengaging the fiducials from each other or from the stylet 430 during normal flexure and manipulation of the cannula body 408 while the fiducials 420 are within the needle lumen 406.

As shown in FIGS. 4A-4B, each successive fiducial 420 may be engaged with the one proximal of it. A pusher stylet 430 may also be disposed through the needle lumen 406. The proximal-most fiducial 420 may be engaged with the stylet 430 in a manner configured substantially similarly to, identical to, or different than the connecting means by which any of the fiducials 420 that are distal of the stylet 430 are engaged with one another. This configuration will allow a user to advance the fiducials 420 distally or retract them proximally while they are attached to each other and to the stylet 430. The engaged fiducials are configured to separatingly disengage when, for example, the first fiducial 440 is angularly offset out of the collinear axis it shares with the second fiducial 450 such that the protrusion 442 is disengaged from the recess 454, as shown in FIG. 4B.

A method of fiducial deployment using the system 400 is described with reference to FIGS. 4A-4B, which show the fiducials 420 engaged with each other and with the stylet 430 by a mechanically interengaged interface. In FIG. 4A, the fiducials 420 are attached together and aligned along a shared collinear axis. In FIG. 4B, the stylet 430 has been advanced distally to deploy the distalmost first fiducial 440. This deployment is effected as the distalmost first fiducial 440 is advanced distally out of the distal aperture 407. As the first fiducial 440 is advanced out of the distal needle aperture 407, it will contact patient tissue and/or be released from the constraint of the lumen 406 such that the fiducial 440 is directed angularly out of the collinear axis it shared with the next fiducial 450, and the connection is undone. This releases and deploys the first fiducial 440 out through the distal needle aperture 407. It should be appreciated that the protrusions and/or recesses of the fiducials of this embodiment may provide added benefits including enhanced echogenicity, engagement with patient tissue that may minimize fiducial migration, and other benefits.

Those of skill in the art will appreciate that a needle including a ramped surface such as the dimple 210 in FIGS. 2A-2B, the ramp 310 in FIGS. 3A-3B, or another needle surface may be implemented with the embodiment of FIGS. 4A-4B. Such an embodiment may facilitate the angular offset of a distalmost fiducial from the next fiducial (or the stylet) to which it is engaged, thus assisting it to be released and deployed. The methods of use for such embodiments will also readily be understood with reference to the present specification and drawings. Embodiments combining these features are contemplated and those of skill in the art will appreciate that such embodiments may be practiced within the scope of the claims.

A method of using a fiducial deployment system may include providing an endoscope, including a working channel. In one preferred method, the endoscope may be configured as an EUS endoscope including a distal ultrasound array configured for ultrasound imaging. An endoscope may also include a video element (e.g., CCD, optical camera, or other means for optical visualization). A method of use may include placing fiducials at the margins of a tumor in a patient's pancreas. As such, an appropriate needle body will be of sufficient length and navigability (e.g., pushability and flexibility) to perorally be directed through a patient's gastrointestinal tract to a target site, including doing so via a working channel of an endoscope such as a gastric endoscope, colonoscope, anuscope, or other visualization/procedure-assisting device.

In one aspect, a fiducial deployment may be accomplished by positioning the distal needle end and a distal-most fiducial of a plurality of fiducials therein at a first target, then retracting the needle while retaining the position of the stylet such that the distal-most fiducial exits the distal aperture of the needle, and remains in a desired first target position. In another aspect, a fiducial deployment may be accomplished by positioning the distal needle terminus and the distal-most fiducial therein adjacent a first target, then holding the needle in position while advancing the stylet such that the distal-most fiducial is advanced past the detent, out of the needle end, and into a desired first target position.

A handle (not shown) may be provided that will provide tactile, auditory, and/or visual indicia regarding deployment of a fiducial. It should be appreciated that, when the stylet is advanced distally, the distal-most fiducial will slide generally easily to the ramp (if present, e.g., dimple 210 or ramp 310). However, a user will likely encounter some resistance as the distal end of the distal-most fiducial engages the ramp and is angularly off-set relative to the collinear axis it shares with more proximal fiducials (particularly in embodiments where this angular offset breaks a mechanical engagement between the two distal-most fiducials. When the needle end is in a desired position, the user can advance the stylet, and thereby the distal-most fiducial, past the ramp into the target site. The stylet and the next fiducial in line will be stopped when the distal end of that next fiducial engages the ramp. In some embodiments, the user may feel decreased resistance as the distal-most fiducial is deployed, and stop pushing the stylet until such time as is desired to deploy that next fiducial in line. Such embodiments will readily be envisioned by one of skill in the art, as will embodiments that may include a handle with visual, tactile, and/or auditory indicia regarding fiducial deployment. The needle may then be repositioned without having to be fully withdrawn from the patient, and the next fiducial deployed in the same manner. It should be appreciated that more or fewer fiducials than are illustrated in the figures herein may be provided in a pre-loaded needle.

It will often be preferred that the fiducials (and distal ramp, if present) be proportioned such that complete deployment of a distal-most fiducial will include it substantially clearing the distal needle terminus and will coincide with the next distal-most fiducial being positioned in a manner ready for deployment. In this manner, a user may efficiently direct a desired number of fiducials to one or more desired locations.

As noted above, after deploying a distal-most fiducial, the user may retract the needle from the first target site, and then direct it to a second target site, where the procedure described above may be repeated. These steps may be repeated for placement of third, fourth, and further fiducials. As is known in the art, these fiducials may be used for "positive targeting" and/or "negative targeting" of a therapy such as radiation therapy ("positive targeting" indicating "treat here", and "negative targeting" indicating "do not treat here"). The present system presents numerous advantages. For example, consider a patient already undergoing an endoscopy procedure to biopsy a located but undiagnosed tissue mass. The endoscopic biopsy can be taken and a tissue slide prepared immediately. If a diagnosis is made (in conjunction with whatever other data are available and pertinent) that the tissue mass will benefit from a treatment where placement of fiducials is indicated, the physician can immediately deploy fiducials in the manner described above, using the same endoscope already positioned for the biopsy.

Figure 5:
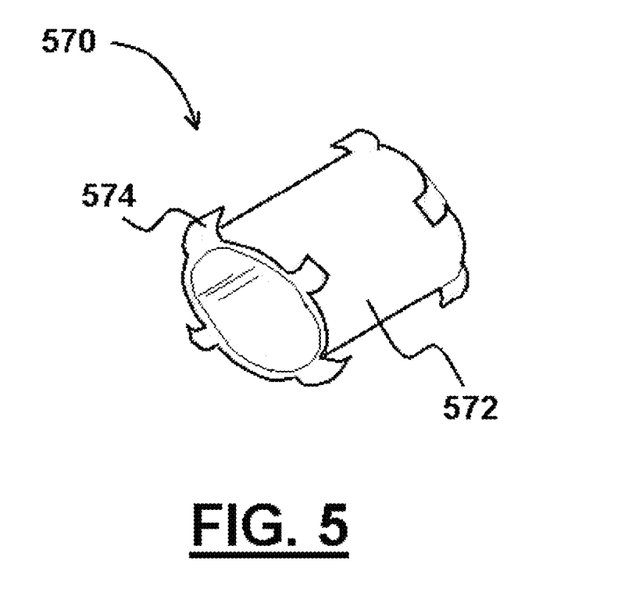
FIGS. 5-6 show embodiments of fiducials useful with fiducial deployment systems.

In other aspects, embodiments may include fiducial embodiments configured to include a tissue-engaging structure. FIG. 5 shows one such embodiment as a fiducial 570. The fiducial 570 may be configured to include a solid, hollow, or partially hollow generally columnar body 572 and at least one radial protrusion 574 extending radially outward from a central body axis. The at least one radial protrusion 574 is embodied here as a plurality of hooked radial protrusions 574. These radially protruding hook structures 574 may provide anti-migration properties for the fiducial 570 when it is deployed in patient tissue, which will be advantageous for targeting treatment. The radially protruding hook structures 574 may also be configured to engage with portion(s) of adjacent fiducials when in a deployment system needle in the manner described above with reference to FIGS. 4A-4B.

Alternatively, or in addition, the radially protruding hook structures 574 and/or the fiducial body 572 may include a rupturable connection to adjacent fiducial(s) in the manner described above with reference to FIGS. 2A-3B. One or more of the structures 574 may extend substantially perpendicular to the body, curve back toward its center, and/or extend in some other direction(s).

Figure 6:
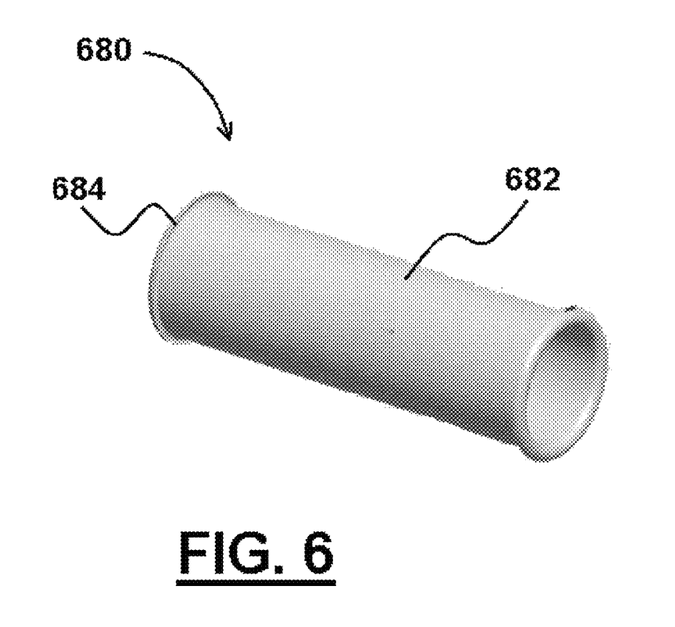

FIG. 6 shows another fiducial 680, also configured to include tissue-engaging structure. The fiducial 680 may be configured to include a solid, hollow, or partially hollow, generally columnar body 682 and at least one radial protrusion 684. The at least one radial protrusion 684 is embodied here as at least one protruding lip 684. This protruding lip structure 684, disposed around at least one end of the fiducial body such that the lip's terminus is oriented away from that fiducial body, may provide anti-migration properties for the fiducial 680 when it is deployed in patient tissue, which will be advantageous for targeting treatment. The radially protruding lip structure(s) 684 may also be configured to engage with portion(s) of adjacent fiducials when in a deployment system needle in the manner described above with reference to FIGS. 4A-4B. Alternatively, or in addition, the radially protruding lip structure(s) 684 and/or the fiducial body may include a rupturable connection to adjacent fiducial(s) in the manner described above with reference to FIGS. 2A-3B.

Drawings and particular features in the figures illustrating various embodiments are not necessarily to scale. Some drawings may have certain details magnified for emphasis, and any different numbers or proportions of parts should not be read as limiting, unless so-designated by one or more claims. Those of skill in the art will appreciate that embodiments not expressly illustrated herein may be practiced within the scope of the present invention, including that features described herein for different embodiments may be combined with each other and/or with currently-known or future-developed technologies while remaining within the scope of the claims presented here.

For example, a needle and fiducials of the present system may be used percutaneously, including in another minimally invasive surgical procedure, such as a laparoscopic-type procedure, within the scope of the claimed invention. For example, a target site may be a location in or near the gastrointestinal tract (e.g., liver, pancreas) such as those locations that may be accessible by endoscopy (using a minimally invasive endoscope introduced through a natural patient orifice, e.g., mouth, anus, vagina). This includes—more broadly—sites reachable through NOTES (natural orifice translumenal endoscopic surgery) procedures. The present method and device may also be used with other minimally-invasive surgical techniques such as percutaneous endoscopic procedures (e.g., laparoscopic procedures) or percutaneous non-endoscopic procedures, but most preferably will be used with less invasive endoscopy procedures. As another example different needle and/or fiducial embodiments disclosed herein may be used with each other and/or with other embodiments enabled by the present disclosure and/or in other disclosures. It is therefore intended that the foregoing detailed description be regarded as illustrative rather than limiting. And, it should be understood that the following claims, including all equivalents, are intended to define the spirit and scope of this invention.

We claim:

1. A fiducial deployment system comprising:
   a needle including
   a generally tubular cannula body defining a needle lumen disposed through at least a lengthwise portion of the cannula body and a distal needle region that includes a distal region aperture opening to the needle lumen, which aperture is configured to allow passage therethrough of a fiducial; and a plurality of fiducials including:

at least one first fiducial and at least one second fiducial, where the at least one first fiducial is engaged with the at least one second fiducial;

where the at least one first fiducial and the at least one second fiducial are disposed along a common collinear axis; and where the distal region aperture, the at least one first fiducial, and the at least one second fiducial are configured such that advancing the at least one first fiducial through the distal region aperture will facilitate complete disengagement of the at least one first fiducial from the at least one second fiducial, such that the second fiducial is separately and independently located apart from the first fiducial;

where engagement of the at least one first fiducial with the at least one second fiducial comprises attachment of the at least one first fiducial to the at least one second fiducial by a non-elastic material, different than the material comprising the at least one first fiducial and the at least one second fiducial, wherein said non-elastic material will separatingly break and disengage the at least one first fiducial away from the at least one second fiducial when the at least one first fiducial is angularly offset from the common collinear axis.

2. The fiducial deployment system of claim 1, configured to separatingly disengage the at least one first fiducial from the at least one second fiducial when the at least one first fiducial and the at least one second fiducial are advanced distally to a predetermined position relative to the needle.

3. The fiducial deployment system of claim 1, where engagement of the at least one first fiducial with the at least one second fiducial comprises attachment of the at least one first fiducial to the at least one second fiducial by a mechanically rupturable material.

4. The fiducial deployment system of claim 1, further comprising at least a third fiducial engaged with the at least one second fiducial and disposed upon the collinear axis shared by the at least one first fiducial and the at least one second fiducial.

5. The fiducial deployment system of claim 1, where the tubular cannula body comprises a lumen-facing surface offset from a surface defining a major length of the lumen, said lumen-facing surface disposed adjacent the distal region aperture, where the lumen-facing surface is configured such that advancing the at least one first fiducial onto the lumen-facing surface directs the at least one first fiducial angularly out of the collinear axis and disengages the at least one first fiducial from the at least one second fiducial.

6. The fiducial deployment system of claim 1, where the distal region aperture is generally coaxial with the needle lumen and generally defines a distal terminus of the cannula body.

7. The fiducial deployment system of claim 1, where the distal region aperture is offset from a longitudinal axis defined by a major length of the needle lumen.

8. The fiducial deployment system of claim 7, where the tubular cannula body comprises a ramp structure that is generally contiguous with and extends into a columnar region generally defined by the needle lumen, where the ramp structure is disposed opposite the distal region aperture and is configured to angularly offset the at least one first fiducial out of the collinear axis, thereby disengaging the at least one first fiducial from the at least one second fiducial, and to direct the at least one first fiducial out through the distal region aperture.

9. The fiducial deployment system of claim 1, further comprising a pusher stylet disposed longitudinally through at least a proximal length of the needle lumen.

10. The fiducial deployment system of claim 9, where a distal end of the pusher stylet is engaged with a proximal-most fiducial of the plurality of fiducials in a manner forming a stylet-fiducial engagement.

11. The fiducial deployment system of claim 10, where the stylet-fiducial engagement is configured substantially similarly to the engagement between the at least one first fiducial and the at least one second fiducial.

12. The fiducial deployment system of claim 1, where at least one of the plurality of fiducials comprises a tissue-engaging structure configured as at least one radial protrusion from a fiducial body of at least one of the plurality of fiducials.

13. The fiducial deployment system of claim 12, where the tissue-engaging structure is configured as at least one hooked protrusion configured to reduce fiducial migration when the at least one of the plurality of fiducials is disposed in patient tissue.

14. The fiducial deployment system of claim 12, where the tissue-engaging structure is configured as at least one protruding lip around at least one end of the fiducial body such that a terminus of the at least one protruding lip is oriented away from the at least one end of the fiducial body and is configured to reduce fiducial migration when the at least one of the plurality of fiducials is disposed in patient tissue.

15. The fiducial deployment system of claim 1, where at least one of the plurality of fiducials comprises a substantially hollow fiducial body.

16. A method of fiducial deployment for placement in a patient, the method comprising:

providing the fiducial deployment system of claim 1;

directing the distal end of the needle to a location near a first target site;

deploying the at least one fiducial at the first target site by:

advancing the at least one fiducial along the common collinear axis and out of the distal region aperture; and disengaging the at least one fiducial from the at least one second fiducial such that the fiducial is disposed at the first target site.

17. The method of claim 16 further comprising:

directing the distal end of the needle to a location near a second target site;

deploying the at least one second fiducial at the second target site by:

advancing the at least one second fiducial along the common collinear axis and out of the distal region aperture; and disengaging the at least one second fiducial from an at least one third fiducial, where the at least one third fiducial is engaged with the at least one second fiducial and disposed upon the collinear axis shared by the at least one first fiducial and the at least one second fiducial.

18. The method of claim 16, where advancing the at least one second fiducial along the common collinear axis will disengage of the at least one fiducial from the at least one second fiducial.

19. The method of claim 16, where advancing the at least one first fiducial along the common collinear axis comprises advancing the at least one first fiducial to a predetermined position relative to the distal region aperture of the needle.

20. The method of claim 16, where engagement of the at least one first fiducial with the at least one second fiducial comprises attachment of the at least one first fiducial to the at least one second fiducial by a mechanically rupturable material, and where the step of disengaging comprises rupturing a material.

21. The method of claim 16, where advancing the at least one first fiducial along the common collinear axis comprises advancing the at least one first fiducial along a ramp structure, where the ramp structure is disposed opposite the distal region aperture and is configured to angularly offset the at least one first fiducial out of the collinear axis, thereby disengaging the at least one first fiducial from the at least one second fiducial.

22. The method of claim 16, where engagement of the at least one first fiducial with the at least one second fiducial comprises a mechanical interlocking engagement, and where the step of disengaging comprises disengaging a protrusion of the at least one first fiducial from a recess of the at least one second fiducial, where prior to disengaging, the protrusion engages the recess.

23. A fiducial deployment system comprising:
a needle including
a generally tubular cannula body defining a needle lumen extending longitudinally through at least a lengthwise portion of the cannula body to a distal region aperture that is open to the needle lumen, which distal region aperture is configured to allow passage therethrough of a fiducial, and
a ramp structure disposed proximate the distal region aperture and extending radially within the needle lumen; and
a plurality of fiducials including:
at least one first fiducial and at least one second fiducial,
where the at least one first fiducial is attached to the at least one second fiducial by a rupturable material different than the material comprising the at least one first fiducial and the at least one second fiducial;
where the at least one first fiducial and the at least one second fiducial are disposed along a common collinear axis; and
where the distal region aperture, the ramp structure, the at least one first fiducial, and the at least one second fiducial are configured such that advancing the at least one first fiducial over the ramp structure will break the rupturable material to completely and separatingly detach the at least one first fiducial from the at least one second fiducial and direct the at least one first fiducial through the distal region aperture, providing for independent deployment of the second fiducial in a different location.

24. A fiducial deployment system comprising:
a needle including
a generally tubular cannula body defining a needle lumen disposed through at least a lengthwise portion of the cannula body and
a distal needle region that includes a distal region aperture opening to the needle lumen, which aperture is configured to allow passage therethrough of a fiducial; and
a plurality of fiducials including:
at least one first fiducial and at least one second fiducial,
where a protrusion of at least one of the at least one first fiducial and the at least one second fiducial mechanically interlockingly engages a recess of the other of the at least one first fiducial and the at least one second fiducial;
where the at least one first fiducial and the at least one second fiducial are disposed along a common collinear axis; and
where the distal region aperture, the at least one first fiducial, and the at least one second fiducial are configured such that advancing the at least one first fiducial through the distal region aperture will enable the at least one first fiducial to disengage from the at least one second fiducial.

25. The fiducial deployment system of claim 24, where engagement of the at least one first fiducial with the at least one second fiducial comprises at least one of the at least one first fiducial and the at least one second fiducial including a protrusion that engages a recess of the other of the at least one first fiducial and the at least one second fiducial.

26. The fiducial deployment system of claim 24, further comprising a distal end of a pusher stylet, disposed longitudinally slidably through the needle lumen, engaged with a proximal-most fiducial of the plurality of fiducials forming a stylet-fiducial engagement configured the same as the interlocking engagement between the at least one first fiducial and the at least one second fiducial.

* * * * *